(12) United States Patent
Yamazaki et al.

(10) Patent No.: US 6,809,331 B2
(45) Date of Patent: Oct. 26, 2004

(54) X-RAY IMAGE READER

(75) Inventors: Hideto Yamazaki, Tokyo (JP);
Toshifumi Yoshida, Tokyo (JP)

(73) Assignee: Rigaku Corporation, Akishima (JP)

( * ) Notice: Subject to any disclaimer, the term of this patent is extended or adjusted under 35 U.S.C. 154(b) by 141 days.

(21) Appl. No.: 10/242,449

(22) Filed: Sep. 13, 2002

(65) Prior Publication Data

US 2003/0053596 A1 Mar. 20, 2003

(30) Foreign Application Priority Data

Sep. 19, 2001 (JP) ........................................ 2001-284702

(51) Int. Cl.[7] ............................................. G03B 42/02
(52) U.S. Cl. ..................................... 250/584; 250/586
(58) Field of Search ................................ 250/584, 586

(56) References Cited

U.S. PATENT DOCUMENTS 6,700,131 B2 * 3/2004 Nishihara et al. ........... 250/586

OTHER PUBLICATIONS

Yamamoto, M., et al., "Development of high–speed Imaging Plate detector." Nuclear Instruments and Methods in Physics Research, Section A, Elsevier, vol. 467–468 (2001), pp. 1160–1162, (Proceedings of the 7th International Conference on Synchrotron Radiation Instrumentation (SRI 2000), Berlin, Germany, Aug. 21–25, 2000.

* cited by examiner

Primary Examiner—Constantine Hannaher
Assistant Examiner—Shun Lee
(74) Attorney, Agent, or Firm—Burns, Doane, Swecker & Mathis, L.L.P.

(57) ABSTRACT

An X-ray image reader including a plurality of read heads and a scan drive device for scanning an X-ray image-storing member by moving the read heads is disclosed. The X-ray image reader has a multi head mode in which a read processing of an X-ray image held on the X-ray image storing member is performed by using at least two of the read heads, and a single head mode in which a read processing of an X-ray image held on the X-ray image storing member is performed by using only one of the read heads. The multi head mode is selected when a high-speed measurement is requested and the single head mode is selected when precise measurement is requested.

16 Claims, 11 Drawing Sheets

X-RAY IMAGE READER

BACKGROUND OF THE INVENTION

1. Field of the Invention

The present invention relates to an X-ray image reader for reading an X-ray image stored in an X-ray image-storing member having an X-ray storing surface formed of, for example, a storage fluorescent member.

2. Description of the Related Art

The X-ray image-storing member formed by a storage fluorescent member has been known. In a case where an X-ray measurement is performed by using such X-ray image-storing member in order to investigate a crystal structure of a specimen, the specimen is irradiated with X-ray and the X-ray image-storing member is exposed by X-ray emitted from the specimen, for example, diffracted X-ray or scattered X-ray. Therefore, a latent image of energy is formed in an X-ray receiving surface of the X-ray image storing member at a coordinates position, which corresponds to a diffraction angle of the diffracted X-ray or the scattered X-ray thus generated.

The storage fluorescent member has the nature of holding a latent image of energy at a position thereof to which X-ray impinges and the nature of converting the latent image of energy into light when a portion thereof which holds the latent image is irradiated with emission stimulating light, such as laser light. Therefore, it is possible to know intensity of X-ray contributed to the formation of the latent image by detecting externally emitted light from the storage fluorescent member when the storage fluorescent member holding the latent image of energy is irradiated by laser light. Further, it is possible to know the diffraction angle of X-ray contributed to the formation of latent image by the coordinates of the storage fluorescent member from which light is emitted.

As an X-ray image reader utilizing the principle mentioned above, the present inventors had proposed a double-head type X-ray image reader 100, which is shown in FIG. 10. In the X-ray image reader 100, a first read head 101a and a second read head 101b are arranged symmetrically about a center axis X0 and laser light from an emitting optical system 102 including a laser light source is divided so that laser light portions are emitted externally through the first and second read heads 101a and 101b, respectively.

Each of the first read head 101a and the second read head 101b can take externally supplied light therein. The light thus taken into the read head is guided to a receiving optical system 103 including a photoelectric converter and then converted into an electric signal by the photoelectric converter.

In order to read an X-ray latent image stored in an X-ray image storing member 104 by using the X-ray image reader 100, the X-ray image storing member 104 takes in the form of a concaved and semi-cylindrical configuration and the center axis X0, which is a rotation center of the first and second read heads 101a and 101b is positioned at substantially a center of the semi-cylindrical X-ray image storing member 104. The first and second read heads 101a and 101b are rotated about the axis line X0 in a direction shown by an arrow A, while the whole X-ray image reader 100 is moved in parallel to the axis line X0 in a direction shown by an arrow B.

With the rotation of the first and second read heads 101a and 101b in the arrow direction A and the straight vertical movement of the whole X-ray image reader in the arrow direction B, the first and second read heads 101a and 101b are alternatively moved to a position opposing to the X-ray image storing member 104, so that a wide area of the X-ray image storing member 104 is scanned by these read heads. In this scanning, laser light from the first read head 101a or the second read head 101b scans a surface of the X-ray image storing member 104 and, when the laser light scans a portion of the surface in which a latent image of energy is formed, fluorescent light is emitted from that portion.

This light is taken in the receiving optical system 103 through the first read head 101a or the second read head 101b and converted into an electric signal, on the basis of a level of which intensity of the light can be obtained. Since the intensity of light corresponds to intensity of X-ray contributed to a formation of the latent image of energy, it is possible to know the intensity of X-ray by measuring the intensity of light.

The conventional double-head type X-ray image reader 100 constructed as mentioned above makes it possible to perform a high speed reading since two read heads 101a and 101b are used alternatively and effectively. However, this double-head type X-ray image reader 100 requires a processing technique for matching the two data obtained alternatively by the read heads 101a and 101b with one reference level. Despite use of such technique a complete processing may not be achieved. Therefore, the conventional double-head type X-ray image reader may not perform a highly precise measurement.

Assuming that there is a difference in output between the first and second read heads 101a and 101b, a correction for compensating for the difference, that is, an intensity correction is required. Further, when the first read head 101a and the second read head 101b are arranged oppositely with an angular interval, which is not exactly 180 degrees, a compensation for the angle error, that is, the angle error correction is necessary.

In general, such corrections are performed by preliminarily reading a reference object by the two read heads, respectively, preliminarily detecting the difference or error from a result of the reading and electrically processing the difference or error thus obtained by using arithmetic operating means, such as a computer. However, it is very difficult to completely connect the measuring results from the two read heads with using the same reference level. This difficulty is not limited to the double-head type X-ray image reader and the same difficulty also exists in a multi-head type X-ray image reader having three or more read heads.

SUMMARY OF THE INVENTION

The present invention was made in view of the above-mentioned problem and an object of the present invention is to provide an X-ray image reader for reading an X-ray image by using a plurality of read heads, which is capable of performing a precise reading.

The object above-mentioned is achieved by the present invention, which is as follows:

(1) An X-ray image reader according to a first aspect of the present invention is featured by comprising a plurality of read heads, scan drive means for scanning an X-ray image storing member by moving the read heads, first control means for performing a process for reading an X-ray image held on the X-ray image storing member by using at least two of the read heads and second control means for performing a process for reading the X-ray image held on the X-ray image storing member by using any one of the read heads.

According to the X-ray image reader of the first aspect of the present invention, it is possible to perform a measurement with using a plurality of read heads, that is, a multi-head mode measurement, by the first control means. Alternatively, it is possible to perform a measurement with using one read head, that is, a single head mode measurement, by the second control means. Therefore, the multi-head mode measurement may be alternatively performed when it is necessary to obtain a result of measurement at high speed regardless of preciseness thereof, that is, when a high-speed measurement is to be performed. On the other hand, the single head mode measurement may be alternatively performed when a precise measurement is to be performed even if the measuring speed is low to some extent.

The single head mode measurement makes it possible to perform a highly precise measurement since there is no situation in which measuring error occurs between the read heads. That is, X-ray image reader according to the present invention makes it possible to perform the highly precise image reading in spite of having the structure for the multi-head mode function.

(2) The scan drive means of the X-ray image reader may drive the read heads to alternatively face them to the X-ray image storing member such that the read heads scan the X-ray image storing member alternatively. In such case, it is possible to perform the high-speed measurement though preciseness of measurement is somewhat degraded.

(3) The scan drive means may include rotary drive means for rotating the read heads and straight drive means for driving the read heads in a direction perpendicular to a plane in which the read heads rotate. In such case, the read heads may be arranged in different angular positions with respect to the rotating direction of the read heads.

According to the X-ray image reader constructed as mentioned above, it is possible to perform a main scan for the X-ray image-storing member in lateral direction by rotating the read heads and, further, to perform a sub scan for the X-ray image storing member by moving the read heads straightly in vertical direction. By such main and sub scans for the X-ray image storing member, it is possible to scan a wide surface of the X-ray image storing member by alternately using the read heads.

(4) The X-ray image-storing member may have an X-ray storing surface formed of a storage fluorescent member. The X-ray image reader may further include a light emitting optical system for emitting emission stimulating light to the read heads and a light receiving optical system for receiving light emitted from the X-ray image storing member through the read heads. The second control means may select one of the read heads as a read head for emitting the emission stimulating light through the light emitting optical system and perform the read processing by use of the read head selected.

X-ray image reader as mentioned above may select the one read head to be used by supplying one of the read heads with emission-stimulating light such as laser light. The one read head thus selected may perform read processing.

Further, the "storage fluorescent member" is a radiation detector capable of storing energy and is also called emission fluorescent member, which is made by forming a film of emission fluorescent member, such as fine crystal of BaFBr:$Er^{2+}$, on a surface of a flexible film, a flat film or other member. The storage fluorescent member has a nature of storing energy of X-ray, etc., and emitting the stored energy as light when it is irradiated with emission stimulating light such as laser light.

That is, when a portion of the storage fluorescent member is irradiated with X-ray, etc., energy thereof is stored in that portion of the storage fluorescent member as a latent image. When the storage fluorescent member is irradiated with emission stimulating light such as laser light, Energy of the latent image is discharged externally as light. It is possible to measure diffraction angle and intensity of X-ray contributed to the formation of the latent image by detecting the thus externally emitted light by means of a photo-tube, etc. Sensitivity of the storage fluorescent member is in the order of 10 to 60 times that of a conventional X-ray film and dynamic range thereof is as wide as $10^6$ to $10^8$.

(5) The second control means may select the one read head, which emits emission-stimulating light, by ON/OFF controlling of the emission stimulating light. With such construction, a mechanical structure of the X-ray image reader becomes simple since the read heads can be selected without necessity of providing a mechanical light shield means such as a beam stopper or a shutter.

(6) Alternatively, the second control means may select the one read head, which emits emission stimulating light, by arranging a beam stopper on an optical path of the light emitting optical system for one of the read heads, which is not used, and arranging no beam stopper on an optical path of the light emitting optical system for the read head, which is used. In this construction of the second control means, it is possible to select a read head without using any complicated electric control system.

(7) According to a second aspect of the present invention, an X-ray image reader comprises a pair of read heads separated from each other by an angle of 180 degrees, rotary drive means for rotating the read heads, straight drive means for moving the read heads in a straight direction perpendicularly to the plane on which the read heads rotate, first control means for reading an X-ray image stored in an X-ray image storing member by using both of the two read heads and second control means for reading the X-ray image stored in the X-ray image storing member by using any one of the two read heads.

The X-ray image reader using two read heads as mentioned above is one so-called double-head type X-ray image reader belonging to the multi-head type X-ray image reader using a plurality of read heads.

In the X-ray image reader according to the second aspect of the present invention, it is possible to perform a measurement with using the two read heads, that is, a double-head mode measurement, by the first control means. Alternatively, it is possible to perform a measurement with using one read head, that is, a single-head mode measurement, by the second control means. Therefore, it is possible to perform the double-head mode measurement when it is necessary to obtain a result of measurement at high speed regardless of preciseness thereof and to perform the single-head mode measurement when a precise measurement is to be performed.

In the single-head mode measurement, it is possible to perform a highly precise measurement since measuring error between the read heads does not occur. That is, the X-ray image reader constructed as mentioned above may perform the highly precise image reading in spite of the double-head mode X-ray image reader which is one kind of a multi-head mode X-ray image reader.

(8) In the X-ray image reader having the double-head mode as mentioned above, X-ray image storing member may have an X-ray imaging surface formed of a storage fluorescent member. The X-ray image reader may further include a light emitting optical system for supplying emission-stimulating light to the two read heads and a light receiving optical system for receiving light emitted from the X-ray image-storing member through the two read heads. The second control means may select one of the read heads as a read head for emitting the emission stimulating light through the light emitting optical system and perform the read processing by any one of the read heads.

In the above-mentioned X-ray image reader, the one read head to be used is selected depending on which read head is supplied with emission-stimulating light, such as laser light The one read head thus selected may perform reading processing.

(9) In the X-ray image reader having the double-head mode as mentioned above, the second control means may select the one read head, which emits emission stimulating light, by ON/OFF controlling the emission stimulating light. With such construction, a mechanical structure of the X-ray image reader becomes simple since the read heads can be selected without necessity of providing a mechanical light shield means such as a beam stopper or a shutter.

(10) Alternatively, in the X-ray image reader having the double-head mode as mentioned above, the second control means may select the one read head, which emits emission stimulating light, by arranging a beam stopper on an optical path of the light emitting optical system for one of the read heads, which is not used, and arranging no beam stopper on an optical path of the light emitting optical system for the read head, which is used. In this construction of the second control means, it is possible to select a read head without using any complicated electric control system.

DETAILED DESCRIPTION OF THE PREFERRED EMBODIMENTS

Figure 1:
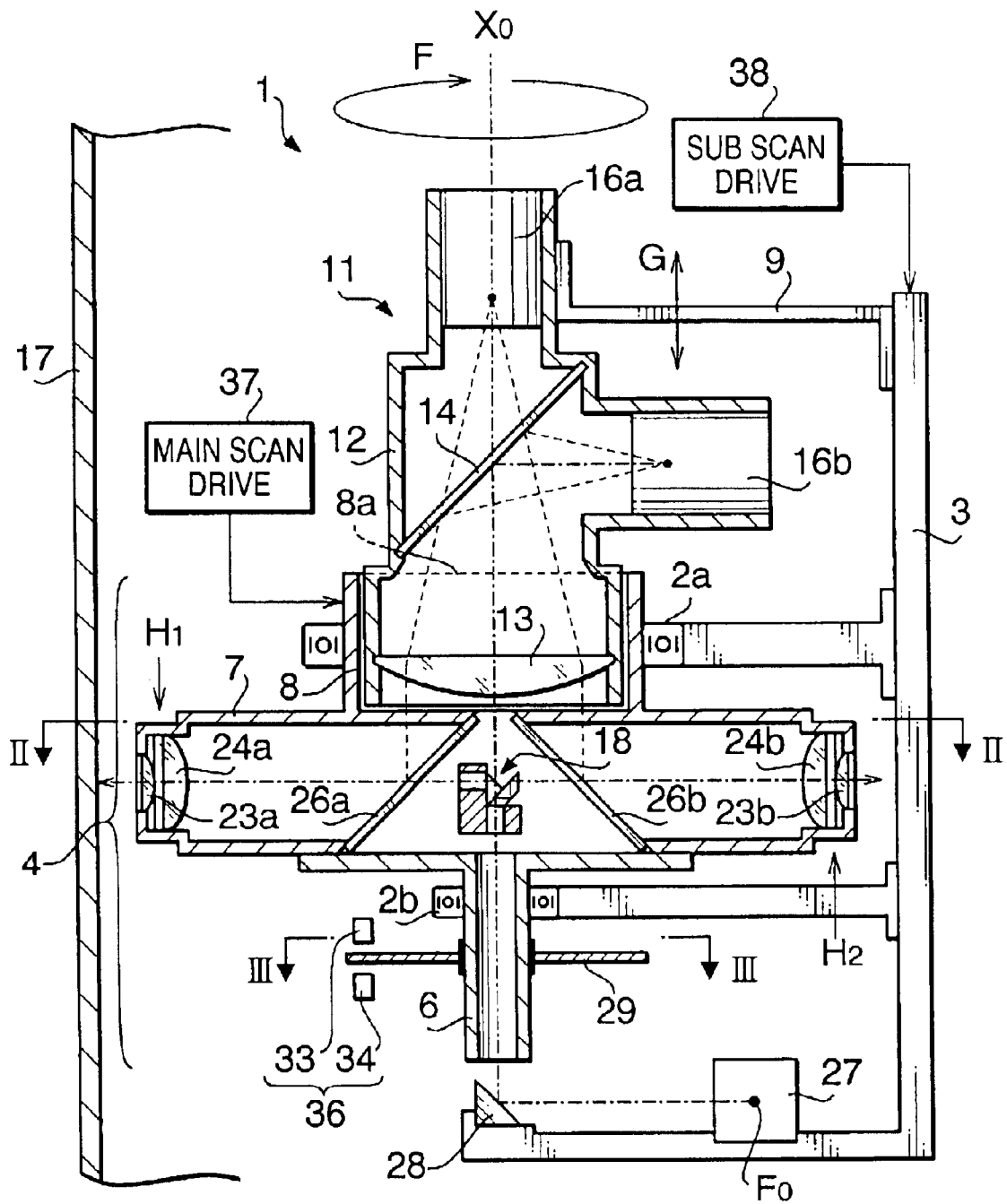
FIG. 1 is a cross sectional view of an X-ray image reader according to an embodiment of the present invention.

The present invention when applied to a double-head type X-ray image reader, which is one of the multi-head type X-ray image reader, will be described with reference to FIG. 1, which illustrates a cross sectional structure of a double-head type X-ray image reader 1 according to the present invention.

The X-ray image reader 1 includes a rotary mechanism 4 rotatably supported by a main frame 3 through bearings 2a and 2b so as to rotate around an axis line X0. An X-ray image-storing member 17 to be read takes in the form of a semi-cylindrical configuration having a center coincident with the axis line X0 as shown in FIG. 2(a), which shows a cross section taken along a line II—II in FIG. 1. The X-ray image-storing member 17 has an X-ray receiving surface formed of a storage fluorescent member.

Figure 2A:
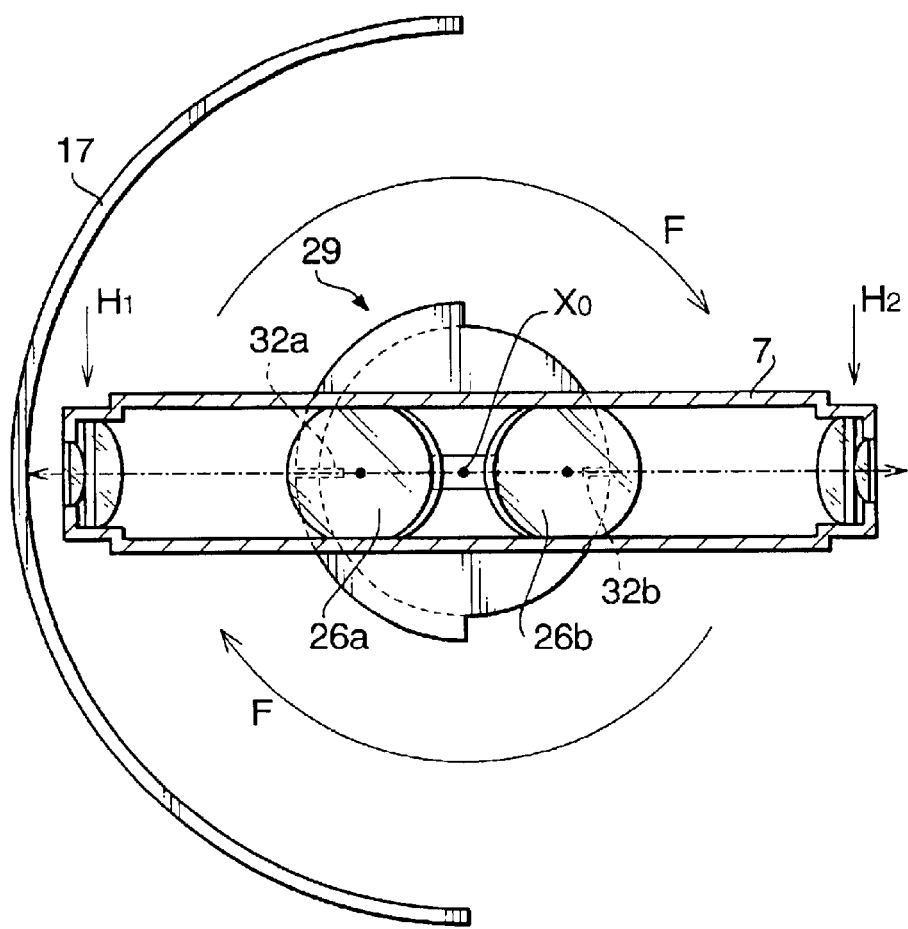
FIG. 2(a) is a cross section taken along a line II—II in FIG. 1.

In FIG. 1, the rotary mechanism 4 includes a cylindrical laser light input portion 6 supported by the bearing 2b, a head portion 7 provided on an upper end portion of the laser light input portion 6 and a cylindrical light output portion 8 provided on an upper surface of the head and supported by the bearing 2a. As is clear from FIG. 2(a), the head portion 7 takes in the form of a long square tube extending in a direction orthogonal to the axis line X0. An upper end portion 8a of the light output portion 8 is opened.

A first read head H1 including lenses 23a and 24a is provided on one end of the head portion 7 and a second read head H2 including lenses 23b and 24b is provided on the other end of the head portion 7. That is, the read heads H1 and H2 are symmetrically arranged on the read portion 7 about the axis line X0 with angular interval of 180 degrees. Although the angular interval of 180 degrees should be set as strictly as possible, there may be deviated from 180 degrees practically. In such case, it is preferable to correct a result of measurement correspondingly to an amount of deviation.

Figure 3:
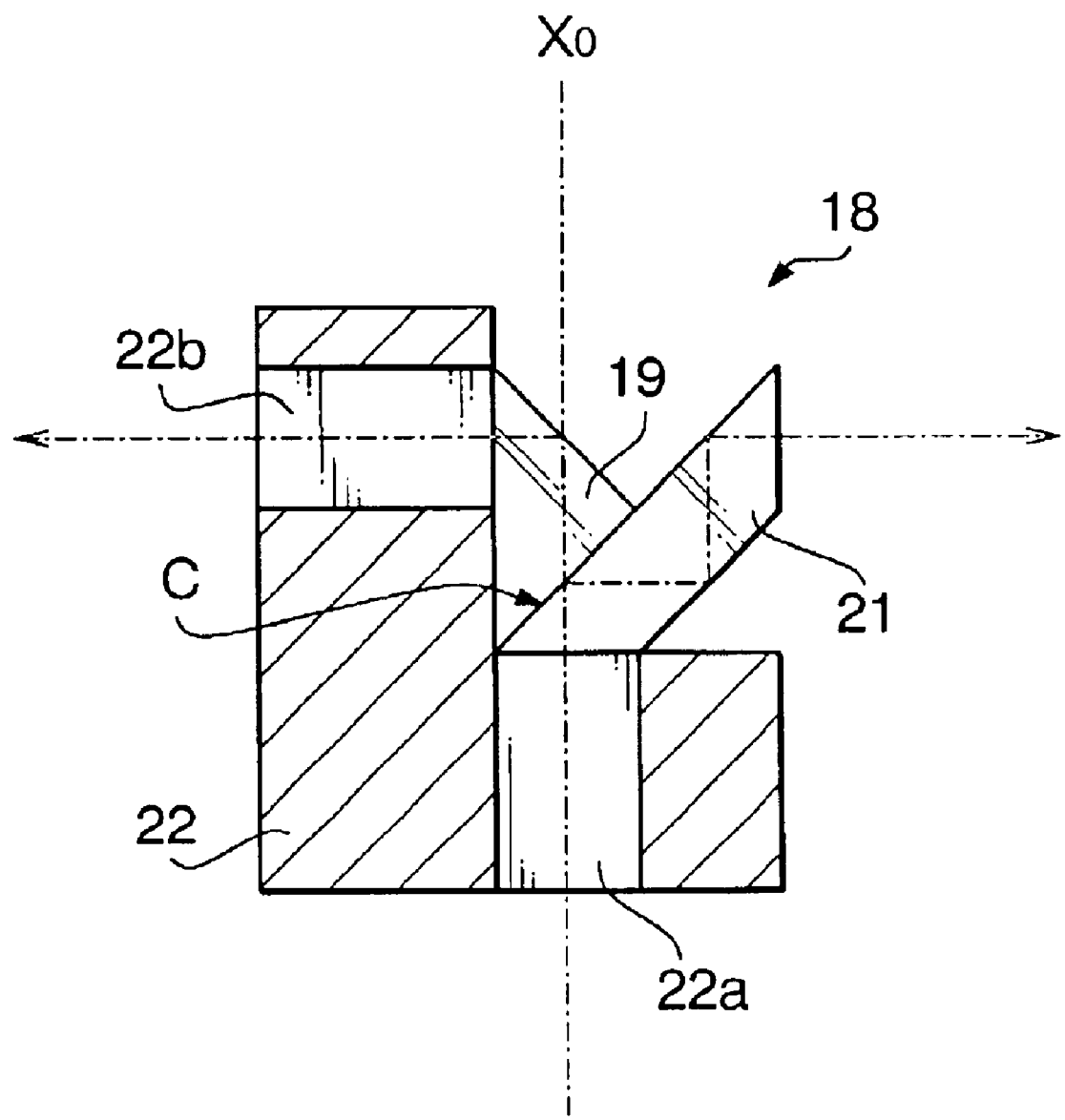
FIG. 3 is a cross section of a beam splitter used in the X-ray image reader shown in FIG. 1.

In FIG. 1, a beam splitter 18 is provided within the head portion 7 and above the laser light input portion 6. The beam splitter 18 is rotated about the axis line X0 integrally with the head portion 7. As shown in FIG. 3, the beam splitter 18 is constructed with a prism 19 having a triangular cross section and a slope surface C, a prism 21 having a trapezoidal cross section and a bottom surface bonded to the surface C of the prism 19 and a base 22 onto which the prisms 19 and 21 are fixed by bonding or other means.

A portion of light inputted through a light input opening 22a formed in the base 22 is transmitted through the interface C between the prisms 19 and 21, and reflected at inner surface of the triangle prism 19 to outputted externally through a light output opening 22b formed in the base 22. The portion of the input light is directed to the first read head H1 in FIG. 1. The other portion of light inputted through the opening 22a is reflected by the interface C, transmitted through the trapezoidal prism 21 and then outputted in a direction opposite to the output direction of the one light portion. The oppositely directed light portion is emitted toward the second read head H2 in FIG. 1.

A dichroic mirror 26a is provided between the first read head H1 and the beam splitter 18 within the head portion 7 and a dichroic mirror 26b is provided between the second read head H2 and the beam splitter 18. Each of the dichroic mirrors allows light from the beam splitter 18 to pass to the corresponding read head. Further, each dichroic mirror reflects light, which is taken in by the corresponding read head to be directed to the beam splitter 18, to a photo-detector 11.

The photo-detector 11 is fixedly supported by the main frame 3 through a bracket 9. The photo-detector 11 includes a frame 12 having a lower end portion loosely fitted in the light output portion 8 of the rotary mechanism 4 and an upper portion supported by the main frame 3 through a bracket 9, a condenser lens 13 provided in a lower end portion of the frame 12, a filter 14 provided on a downstream of the condenser lens 13 in a propagation direction of light (meaning above the condenser lens 13 in FIG. 1), a first photo-tube 16a provided above the filter 14 to receive light transmitted therethrough and a second photo-tube 16b provided to receive light reflected by the filter 14.

Since the lower end portion of the photo-detector 11 is loosely fitted in the light output portion 8 of the rotary mechanism 4, the photo-detector 11 can be maintained stationary even when the rotary mechanism 4 is rotated. The filter 14 may be formed of a typical transparent member such as glass plate and functions to pass about 90% of incident light therethrough and guide it to the first phototube 16a and to reflect the remaining light to the second phototube 16b. The phototubes 16a and 16b are opto-electric conversion elements having known structure and function to output electric signals corresponding to intensities of lights incident thereon.

The X-ray image reader 1 further includes a laser light generator 27 having a laser light source Fo therein. The laser light generator 27 emits laser light when a power source thereof is turned ON and stops the emission of laser light by turning the power source OFF. A prism 28 is provided below the laser light input portion 6 of the rotary mechanism 4. The laser light emitted from the laser light generator 27 is reflected by the prism 28 and taken in the laser light input portion 6.

Figure 2B:
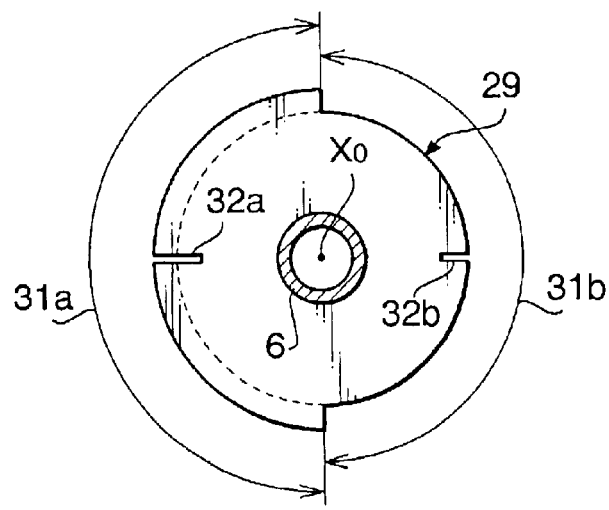
FIG. 2(b) is a cross section taken along a line III—III in FIG. 1.

A rotary disk 29 for generating pulse signal is provided at a suitable position on an outer peripheral surface of the laser light input portion 6. As shown in FIG. 2(b), the rotary disk 29 takes in the form of a circular disk including a semi circular large diameter portion 31a and a semi circular small diameter portion 31b.

A first slit 32a is formed in substantially a center of an outer periphery of the large diameter portion 31a and extends to the axis line X0 by a limited length and a second slit 32b is formed in substantially a center of an outer periphery of the large diameter portion 31b and extends to the axis line X0 by a length slightly shorter than the length of the slit 32a so that radial positions of bottoms of the slits 32a and 32b become substantially equal. As shown in FIG. 2(a), the first slit 32a corresponds in position to the first read head H1 and the second slit 32b corresponds to the second read head H2.

Further, in FIG. 1, a sensor 36 composed of a light-emitting element 33 and a light-receiving element 34 is provided at a suitable position with respect to the periphery of the rotary disk 29. The sensor 36 distinguishes the first and second slits 32a and 32b on the basis of the difference in diameter between the large and small diameter portions 31a and 31b of the rotary disk 29 when the rotary mechanism 4 rotates, that is, when the first and second read heads H1 and H2 rotate, and outputs electric signals correspondingly thereto.

Figure 5:
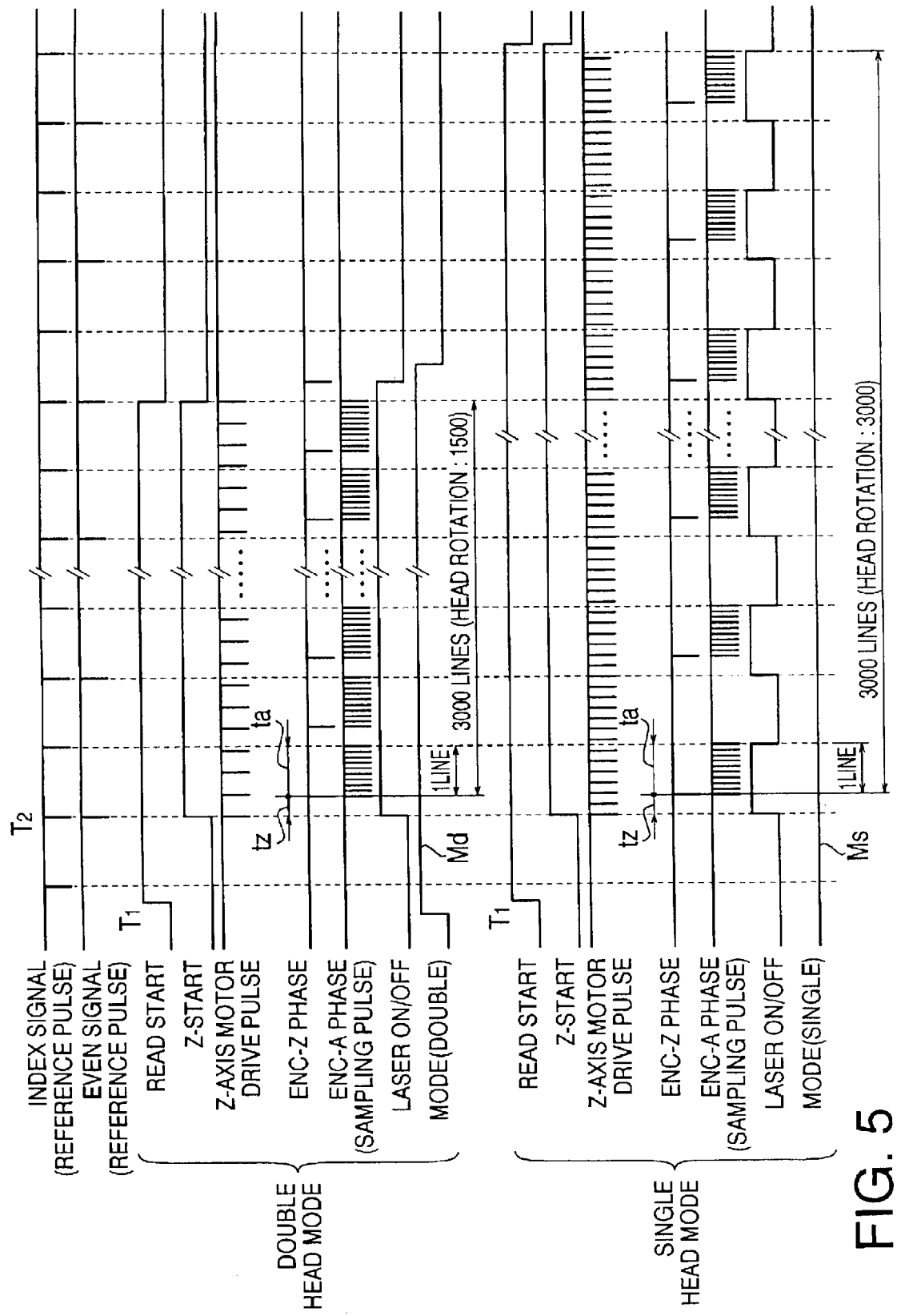
FIG. 5 is a timing chart of a control to be executed by the electric control system shown in FIG. 4.

In concrete, the sensor 36 generates an index signal pulse and an EVEN signal pulse in a timing chart shown in FIG. 5 as reference pulses. The index pulse is generated every half rotation of each of the first and second read heads H1 and H2, that is, at every time when each of the read heads H1 and H2 rotates by 180 degrees. The EVEN pulse is generated every time when the rotary mechanism 4 makes one rotation, that is, rotates by 360 degrees. That is, the EVEN pulse is generated at a time when the rotary mechanism 4 rotates by 360 degree, 720 degrees, 1080 degrees and so on. In this embodiment, the EVEN pulse is generated when the first read head H1 scans the X-ray image-storing member 17.

In FIG. 1, a main scan rotary drive 37 is connected to the rotary mechanism 4 including the first and second read heads H1 and H2. The main scan rotary drive 37 rotates the read heads H1 and H2 about the axis line X0 to scan the X-ray image storing member 17 laterally in a main scan direction in a plane perpendicular to the axis line X0.

The main scan rotary drive 37 may be constructed with a drive system having an arbitrary structure. For example, the drive system may be constructed with a motor such as a pulse motor or a servomotor whose rotation speed can be controlled as a drive source and a power transmission system constructed with such as belt and gears for transmitting the rotation of the motor to the rotary mechanism 4.

Further, a sub scan drive 38 for sub-scanning the X-ray image storing member 17 is connected to the main frame 3, which supports the whole X-ray image reader 1. The sub scan drive 38 moves the main frame 3 in a sub scan direction parallel to the axis line X0 to move the read heads H1 and H2 in a longitudinal direction to thereby scan the X-ray image storing member 17 in the sub scan direction.

The sub scan drive 38 may be constructed with a driving system having an arbitrary structure. For example, the sub scan drive 38 may be constructed with a drive source including a motor whose rotation speed can be controlled, such as pulse motor or servo motor and power conversion means, which may include a lead screw, for converting rotation into straight movement.

In this embodiment shown in FIG. 1, the light emitting optical system is constructed with a combination of the laser light generator 27, the prism 28, the beam splitter 18 and the first read head H1 and a combination of the laser light generator 27, the prism 28, the beam splitter 18 and the second read head H2, respectively. The light receiving optical system is constructed with a combination of the first read head H1, the dichroic mirror 26a and the photo detector 11 and a combination of the second read head H2, the dichroic mirror 26b and the photo detector 11, respectively.

Figure 4:
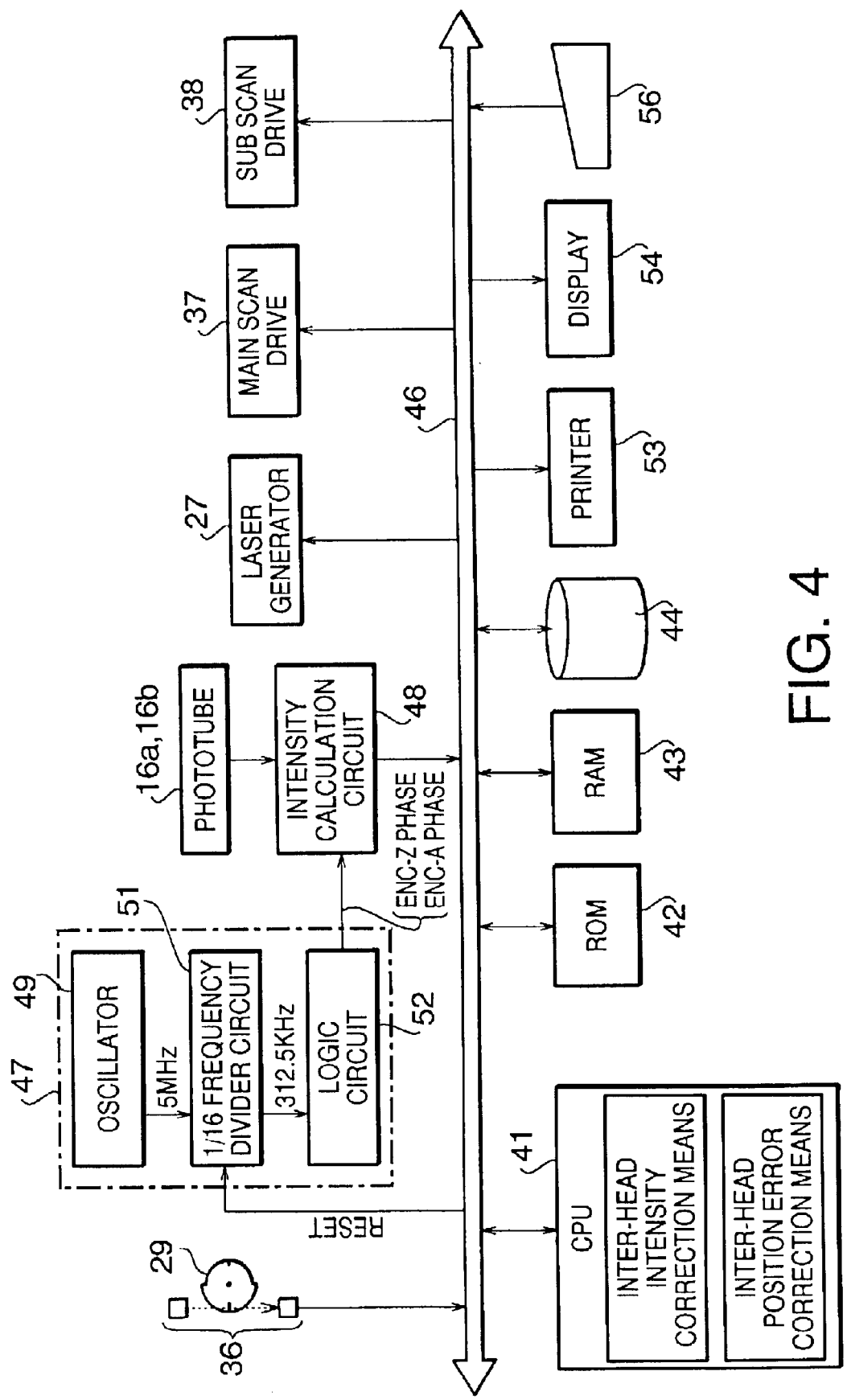
FIG. 4 is a block diagram showing an example of an electric control system used in the X-ray image reader of the present invention.

FIG. 4 shows an embodiment of a control system for controlling the operation of the X-ray image reader 1 shown in FIG. 1. This control system is constructed with a computer system including a CPU (Central Processing Unit) 41, a ROM (Read Only Memory) 42, a RAM (Random Access Memory) 43, an information memory 44 and a bus 46 for connecting them mutually.

To the bus 46, an output terminal of the sensor 36 provided in the vicinity of the rotary disk 29 as shown in FIG. 1 for confirming an angular position of the read head, a RESET terminal of a pulse generator circuit 47, an output terminal of an intensity calculation circuit 48, an ON/OFF signal input terminal of the laser light generator 27 as shown in FIG. 1, a control signal input terminal of the main scan rotary drive 37 as shown in FIG. 1 and a control signal input terminal of the sub scan drive 38 are connected. Further, output devices such as a printer 53 and a display 54, etc., and an operational input device 56 including a keyboard and a mouse, etc., are connected to the bus 46.

The pulse generator circuit 47 includes an oscillator 49 capable of generating a stable pulse signal, a frequency divider circuit 51 for dividing an output frequency of the oscillator 49 by, for example, 16 and a logic circuit 52 for producing a pulse signal suitable for use in the control system of this embodiment from the output pulse signal of the frequency divider circuit 51. The oscillator 49 may be, for example, a crystal oscillator or a CR oscillator capable of generating a pulse signal having very stable frequency. The stability of frequency of the pulse signal obtained from the oscillator 49 is very high compared with that of a pulse signal, which is obtained from a commercially available encoder mounted on the rotary mechanism 4, correspondingly to rotation thereof.

The oscillator 49 may output a pulse signal having frequency of, for example, 5 MHz and the frequency divider circuit 51 generates a pulse signal having frequency of, for example, 312.5 KHz by dividing the oscillator frequency. Incidentally, the frequency divider circuit 51 outputs the pulse signal by using, as a reference, a time when a RESET signal is inputted to its RESET terminal. The logic circuit 52 generates pulse signals in ENC (meaning Encode)-Z phase and ENC-A phase shown in FIG. 5 on the basis of the output pulse of the frequency divider circuit 51 and outputs these pulse signals to the intensity calculation circuit 48.

The ENC-Z phase pulse is generated when a predetermined number (for example, 122) of the output pulse signals of 312.5 kHz of the frequency divider circuit 51 are counted from a time when the reset signal is inputted to the RESET terminal of the frequency divider circuit 51. As shown in FIG. 5, a time period tZ of the ENC-Z phase pulse is set to 400 μS corresponding to 122 pulses. The time period of 400 μS is enough to stabilize the laser output after the laser light generator 27 is activated in response to the ON signal, when the laser light generator 27 repeats the ON/OFF operation intermittently in a single head mode operation thereof, which is to be described later.

Figure 6:
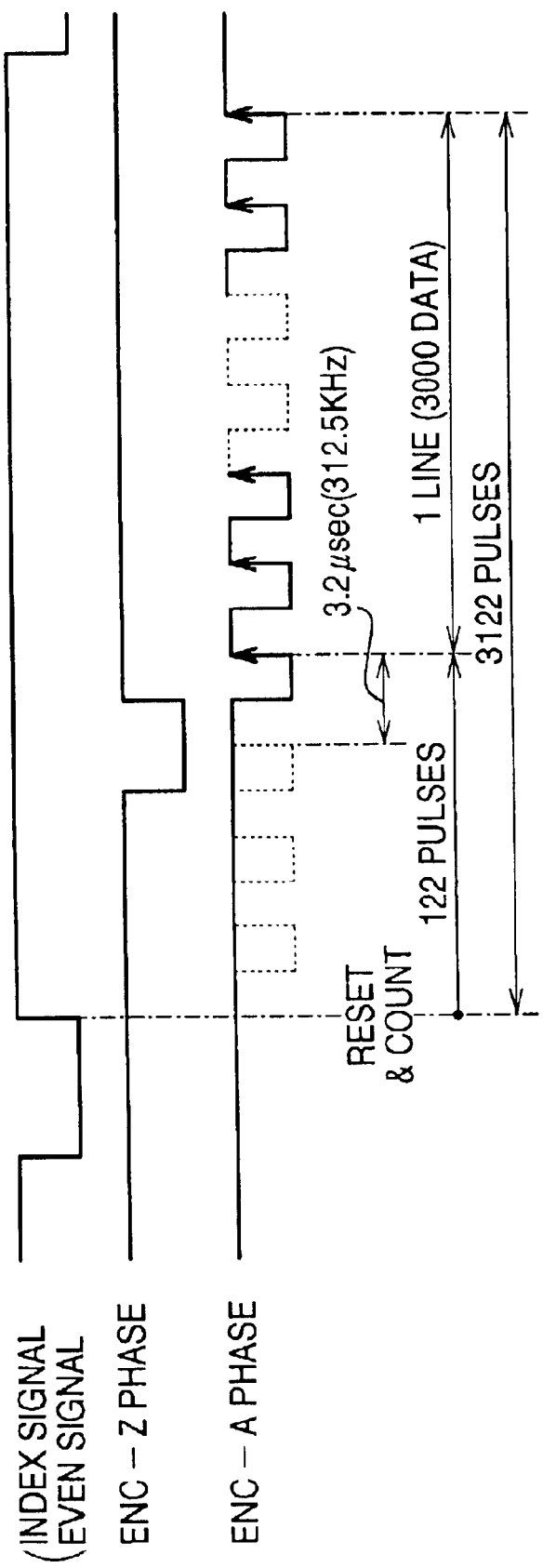
FIG. 6 is a timing chart showing a main portion of the control shown in FIG. 5.

The ENC-A phase pulse has the same frequency of 312.5 KHz as that of the frequency divider circuit 51 and is outputted during a time period from the generation of the ENC-Z phase pulse to a time at which the RESET signal is inputted to the frequency divider circuit 51. In this embodiment, the RESET signal is supplied to the frequency divider circuit 51 when the index signal or the EVEN signal is outputted from the angle sensor 36. FIG. 6 shows a relation of the ENC-A phase pulse and the ENC-Z phase pulse to the index signal or the EVEN signal. In this embodiment, 3000 pulses are outputted at 312.5 KHz as the ENC-A phase signal. The 3000 pulses correspond to a scan area for 1 line of the main scan by the first read head H1 and the second read head H2.

In FIG. 4, the intensity calculation circuit 48 calculates the intensity of light emitted from the X-ray image storing member 17 (see FIG. 1), and hence the intensity of energy of the latent image formed in the X-ray image storing member 17, and hence the intensity of X-ray contributed to the formation of the latent image of energy by counting the output pulses of the first phototube 16a or the second phototube 16b as shown in FIG. 1 respectively.

Incidentally, in this embodiment, 90% of light incident on the optical filter 14 is taken in by the first phototube 16a and 10% thereof is taken in by the second phototube 16b. When the amounts of light taken in by the phototubes 16a and 16b are not excessive, the processing is performed on the basis of the electric signal obtained by the first phototube 16a, which receives 90% of the light.

On the other hand, when the amounts of light taken in by the phototubes 16a and 16b are excessive, the processing is performed on the basis of the electric signal obtained by the first phototube 16b, which receives 10% of the light. This is because, when the light amounts are excessive, there may be a case where the output of the first phototube 16a becomes too large to operate the electric circuits belonging to the first phototube 16a normally.

In FIG. 4, the intensity calculation circuit 48 samples the output signal of the phototubes 16a and 16b every pulse of the 3000 pulses outputted by the logic circuit 52. That is, the intensity calculation circuit 48 reads the output of the phototube 16a or 16b during 1 pulse period and outputs the output of the phototube thus read as a read value of 1 pixel. The read value of 1 pixel is stored in a predetermined memory position in the RAM 43 shown in FIG. 4.

Alternatively, it may be possible to determine the read value of 1 pixel by providing an AD converter in the intensity calculation circuit 48, sampling the output of the phototube 16a or 16b by a plurality of times, for example, 8 times within 1 pulse period, converting the sample values into digital values and integrating the digital values.

In FIG. 4, the information storage medium 44 is usable by a computer to store an information such as programs and data, etc., and may be realized by an optical disk such as CD (meaning Compact Disc), DVD (meaning Digital Video Disc), an opto-magnetic disk such as MO (meaning Magnet Optical), a magnetic disk, a hard disk, a magnetic tape or a semiconductor memory such as a ROM. Incidentally, it is usual that a portion or whole portion of the information stored in the information storage medium 44 is transferred to the RAM 43 when the power source of the system is turned ON.

The ROM 42 stores, for example, the system program (meaning initializing information of the system, etc.). The RAM 43 is used as a working area of the CPU 41, or temporally stores contents of the information storage medium 44 and/or the ROM 42, a calculation result of the CPU 41 and/or information from input/output devices such as the intensity calculation circuit 48.

According to the program stored in the information storage medium 44 and/or the information inputted from the operational input device 56, the CPU 41 controls the operation of various input/output devices connected to the bus 46 and performs an arithmetic operation for correcting the output signal of the intensity calculation circuit 48 and various data processing. Incidentally, in a case where the system shown in FIG. 4 is used as one of users constructing a network, a network driver and a communication portion are connected to the bus 46 for connection to a host or other network users through the network driver, etc.

The program used in this embodiment includes a routine for executing a double head mode by the CPU 41 and a routine for executing a single head mode by the CPU 41. Both the first and second read heads H1 and H2 are used in the double head mode and either one of the first and second read heads H1 and H2 is used in the single head mode. The respective modes will be described.

Incidentally, the processing, such as the exposure processing, for forming the latent image of energy in the X-ray image storing member 17 shown in FIG. 1 and FIG. 2 is performed prior to the image reading processing. There are various exposing systems, one of which is the exposure with using an X-ray measuring system such as shown in FIG. 11.

Figure 11:
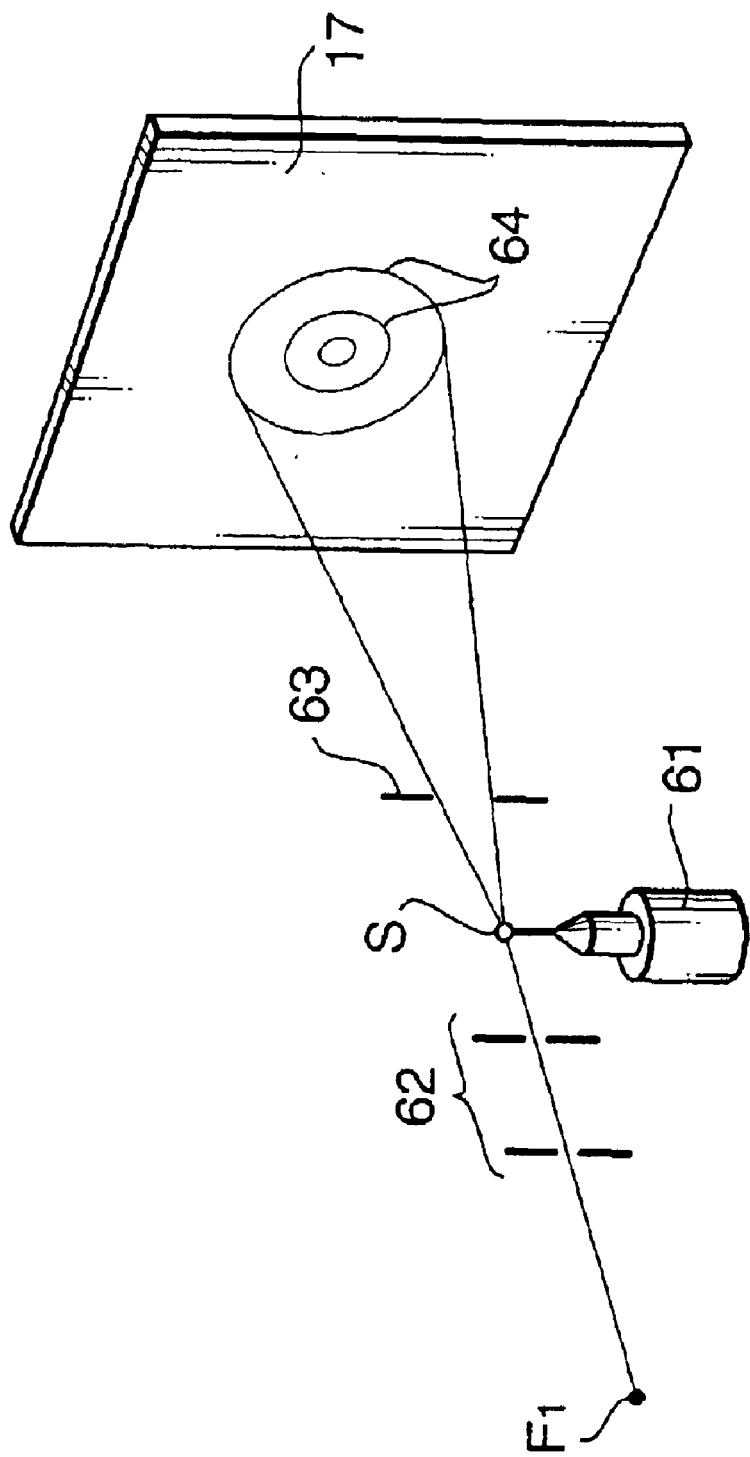
FIG. 11 illustrates an example of an X-ray measuring device for preliminarily measuring X-ray prior to the read measurement by using the X-ray image reader according to the present invention.

In the X-ray measuring system shown in FIG. 11, a goniometer head 61 supports a specimen S, which is to be investigated on its internal crystal structure, etc. X-ray emitted and diverging from an X-ray source $F_1$ is directed to the specimen S by a pinhole collimator 62. Thus, the specimen S is irradiated with the X-ray. When the specimen S is irradiated with the X-ray, diffracted X-ray or scattered X-ray occurs from the specimen S correspondingly to the internal crystal structure of the specimen S. The diffracted or scattered X-ray from the specimen S is limited on its cross sectional area by a divergence limiting slit 63 to be incident on an X-ray receiving surface, namely a surface made of storage fluorescent member, of the X-ray image storing member 17. Thus, the X-ray receiving surface is exposed with the X-ray.

With this X-ray exposure, a latent image of energy is formed at a coordinates of the X-ray receiving surface of the X-ray image storing member 17, which corresponds to diffraction angle of the diffracted X-ray, that is, to the internal crystal structure of the specimen S. Assuming the specimen S being composed of powder, Debye rings 64 are stored as the latent image of energy. With respect to the X-ray image-storing member 17 holding the latent image in such way, the X-ray image reader 1 shown in FIG. 1 performs a reading process for the latent image in either the double head mode or the single head mode as described in the following.

(Double Head Mode)

When a measurement of the X-ray image storing member 17 having the latent image in the diffraction angular position corresponding to the crystal structure of the specimen S is to be performed by the measuring system shown in FIG. 11 at high speed regardless of preciseness of the measurement, an operator selects the double head mode of the X-ray image reader 1 shown in FIG. 1.

In concrete, the operator instructs the CPU 41 of the double head mode measurement through the operational input device 56. In such state, when the operator instructs a start of reading operation at a timing T1 in the timing chart shown in FIG. 5, the CPU 41 sets the operation mode of the computer to the double head mode Md.

In response to the read start at the timing T1, the CPU 41 activates the main scan rotary drive 37 as shown in FIG. 1 to rotate the rotary mechanism 4 to thereby rotate the first and second read heads H1 and H2 about the axis line X0. Rotation speed at this moment is preliminarily set to a predetermined value and the CPU 41 controls the main scan rotary drive 37 in such a way that the rotation speed is maintained at the predetermined rotation speed.

With the rotation of the first and second read heads H1 and H2, the sensor 36 as shown in FIG. 1 outputs the index signal and the EVEN signal such as shown in FIG. 5. The index signal is outputted every time when the first and second read heads H1 and H2 rotate in the direction shown by the arrow F by 180°, respectively. The EVEN signal is outputted every time when the first read head H1 rotates in the direction F by 360°.

Thereafter, at a timing T2 in FIG. 5, the laser light generator 27 as shown in FIG. 1 is instructed to start laser light emission. Simultaneously therewith, a Z axis motor drive pulse signal is supplied to the sub scan drive 38 as shown in FIG. 1 to move the whole X-ray image reader 1 vertically to thereby move the first and second read heads H1 and H2 in a direction shown by an arrow G parallel to the axis line X0. Speed of the straight movement of the read heads H1 and H2 is controlled to a constant value V, which is determined by the pulse width of the Z-axis motor drive pulse signal.

Figure 7:
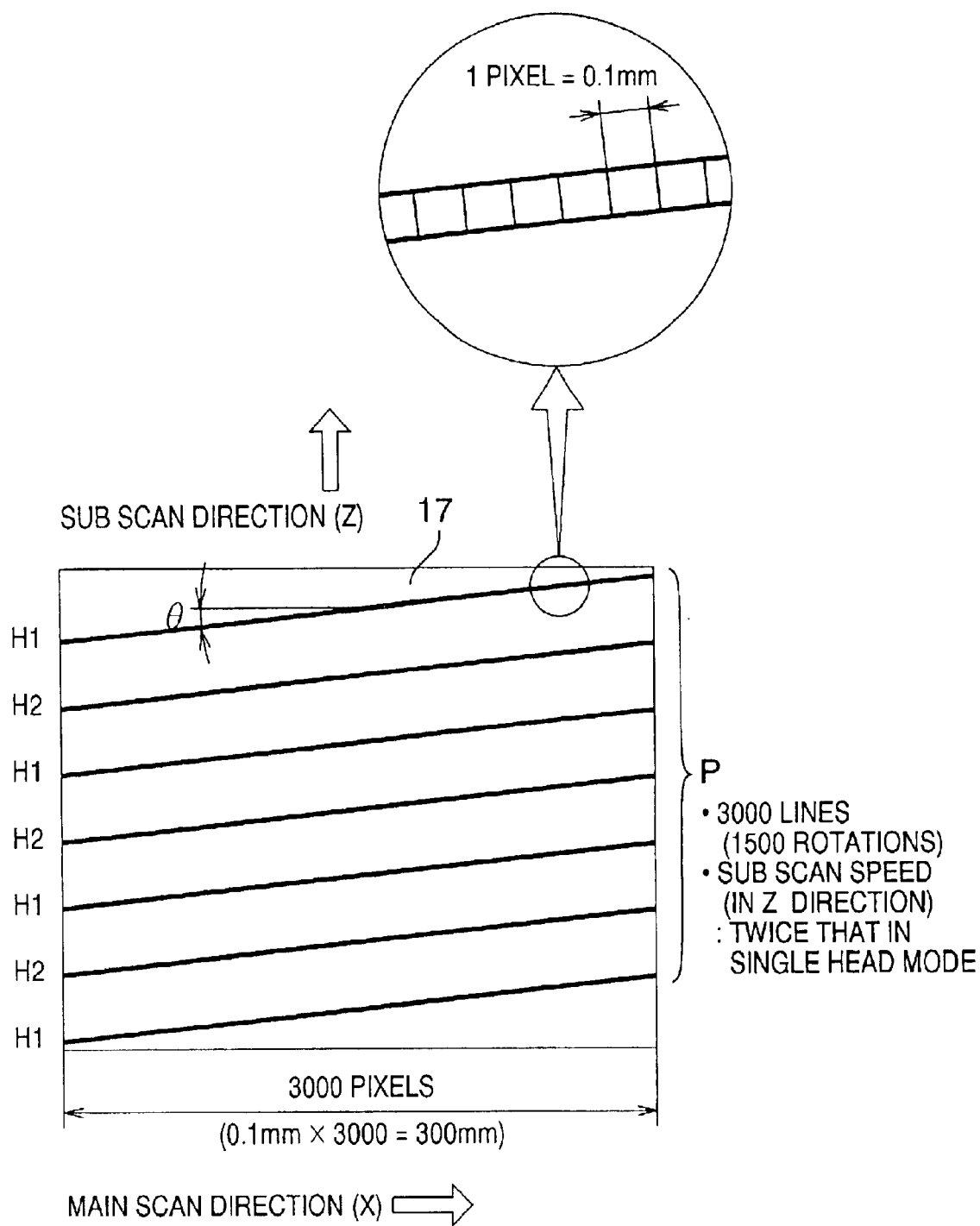
FIG. 7 illustrates a read scanning in a double-head mode operation of the X-ray image reader.

When the first and second read heads H1 and H2 perform the main scan of the X-ray image storing member 17 by rotating in the direction shown by an arrow F, while performing the sub scan by moving straight in the direction shown by an arrow G, the X-ray image storing member 17 is helically scanned by the first and second read heads H1 and H2, which come thereto alternatively as shown by P in FIG. 7.

The number of scan lines is set to, for example, 3000. In the double head mode, two scan lines are formed by the first and second read heads H1 and H2 when the rotary mechanism 4 is rotated one time. Therefore, it is possible to form 3000 scan lines by rotating the rotary mechanism 1500 times.

During the scanning of the X-ray image storing member 17 by the read heads H1 and H2, laser light from the laser light generator 27 as shown in FIG. 1 is reflected by the prism 28 to the laser light input portion 6 of the rotary mechanism 4 and then divided to the first and second read heads H1 and H2 by the beam splitter 18.

When either one of the first and second read heads H1 and H2 scans the X-ray image storing member 17, the laser light supplied to the one read head passes therethrough and exposes the X-ray image storing member 17 along the scan lines P shown in FIG. 7. When a latent image of energy exists in the exposed portion of the X-ray image-storing member 17, the energy is excited by the laser light and emitted externally as light. Then, the light emitted from the X-ray image-storing member 17 is received by one of the first and second read heads H1 and H2.

The light received by the read head is reflected by the dichroic mirror 26a or 26b in the head portion 7 of the rotary mechanism 4 to the first and second phototubes 16a and 16b of the photo detector 11 and then signals corresponding to the lights are outputted from output terminals of the phototubes.

In the period during which the X-ray image storing member 17 is irradiated with laser light, the RESET signal is transmitted to the RESET terminal of the frequency divider circuit 51 of the pulse generator circuit 47 as shown in FIG. 4 correspondingly to the index signal outputted every half rotation of the first and second read heads H1 and H2 as shown in FIG. 5, and so single ENC-Z phase pulses and successive ENC-A phase pulses are outputted to the output terminal of the logic circuit 52.

The ENC-Z phase pulse is generated after a time period $t_z$ of the generation of the index signal. On the other hand, the ENC-A phase pulse is successively generated in a time period from the generation of the ENC-Z phase pulse to a generation of a next index signal, that is, a time period during which the first read head H1 or the second read head H2 makes a half rotation which corresponds to an angle of 180 degrees. The frequency of the ENC-A phase pulse signal is 312.5 KHz, which is the output frequency of the frequency divider 51 shown in FIG. 4, and includes 3000 pulses during the half rotation of the read head corresponding to one scan line as shown in FIG. 6.

The intensity calculation circuit 48 shown in FIG. 4 reads the output of the phototube 16a or 16b for every pulse of the ENC-A phase pulse signal from the logic circuit 52. The read value is stored in a predetermined region of the RAM 43. In this manner, data for 1 pixel corresponding to one pulse of the ENC-A phase pulse signal is sampled. In this embodiment, the width of 1 pixel corresponds to 0.1 mm as shown in FIG. 7. Since 3000 pulses of the ENC-A phase pulse signal are outputted for 1 scan line, the intensity calculation circuit 48 samples data for 3000 pixels obtained by dividing 1 scan line by 3000.

When the read head H1 or H2 comes in the position opposing to the X-ray image storing member 17 again after the data for 3000 pixels related to 1 scan line is sampled, data of 3000 pixels related to a next scan line in the sub scan direction is sampled by that read head. Subsequently thereto, the data sampling is performed alternatively by the first and second read heads H1 and H2 for every scan line, resulting in that the data for 3000 scan lines in the sub scan direction are sampled.

The light intensity data of the whole area of the measuring region of the X-ray image storing member 17 is read out as shown in FIG. 7 and the data is stored in a predetermined region of the RAM 43 correspondingly to the coordinates values of the X-ray image storing member 17 in the form of a data table. The data table is nothing but the read result of the latent image of energy stored in the X-ray image-storing member 17. The data table is displayed on a screen of the display 54 or printed out on a recording sheet such as a printing paper by the printer 53, according to necessity, under control of the CPU 41.

As mentioned, in the double head mode, the reading operation is performed by alternatively using the first and second read heads H1 and H2. In this case, the reading characteristics of the first read head H1 is not always identical to that of the second read head H2.

For example, an output level of the phototube 16a or 16b when the X-ray image storing member 17 is read by using the first read head H1 is not always the same as that when the X-ray image storing member 17 is read by using the second read head H2. Further, although, in FIG. 2(a), the first read head H1 and the second read head H2 must be strictly arranged with an angular interval of 180 degrees fundamentally, it is practical that the interval may be deviated from 180 degrees due to matching error and/or assembling error of the X-ray image reader 1.

Therefore, it is impossible to obtain highly precise read data unless some correction is performed between the read data obtained by using the first read head H1 and that obtained by using the second read head H2. In this embodiment, the CPU 41 shown in FIG. 4 preliminarily acquires a difference in reading characteristics between the first and second read heads H1 and H2 by executing the reading of the same object to be measured as data and stores the latter data in the RAM 43 as correction data.

After the read data are obtained by performing the measurement with using both the first and second read heads H1 and H2, a process for matching the read data is performed by correcting the read data in software on the basis of the preliminarily stored correction data. Thus, it is possible to improve the reliability of the read data obtained by using different read heads. That is, the CPU 41 functions as an inter-head intensity correcting means for compensating for error in intensity between the read heads and as an interhead positional deviation correcting means for compensating for deviation of the angular position between the read heads.

(Single Head Mode)

When a measurement of the X-ray image storing member 17 having the latent image in the diffraction angular position corresponding to the crystal structure of the specimen $\underline{S}$ is to be performed by the measuring system shown in FIG. 11 with high precision regardless of the measuring speed, an operator selects the single head mode of the X-ray image reader 1 shown in FIG. 1.

In concrete, the operator instructs the CPU 41 of the single head mode measurement through the operational input device 56. In such state, when the operator instructs a start of reading operation at a timing T1 in the timing chart shown in FIG. 5, the CPU 41 sets the operation mode of the computer to the single head mode Ms.

In response to the read start at the timing T1, the CPU 41 activates the main scan rotary drive 37 as shown in FIG. 1 to rotate the rotary mechanism 4 to thereby rotate the first and second read heads H1 and H2 about the axis line X0. Rotation speed at this moment is preliminarily set to the same predetermined value as used in the double head mode.

With the rotation of the first and second read heads H1 and H2, the sensor 36 as shown in FIG. 1 outputs the index signal and the EVEN signal such as shown in FIG. 5 as in the case of the double head mode.

Thereafter, at a timing T2 in FIG. 5, the laser light generator 27 as shown in FIG. 1 is instructed to start laser light emission. Simultaneously therewith, a Z axis motor drive pulse signal is supplied to the sub scan drive 38 as shown in FIG. 1 to move the whole X-ray image reader 1 vertically to thereby move the first and second read heads H1 and H2 in a direction shown by an arrow $\underline{G}$ parallel to the axis line X0. Speed of the straight movement of the read heads H1 and H2 is controlled to a constant value, which is a half of the speed $\underline{V}$ in the case of the double head mode, by making the pulse width of the Z axis drive pulse a half of that in the case of the double head mode.

Figure 8:
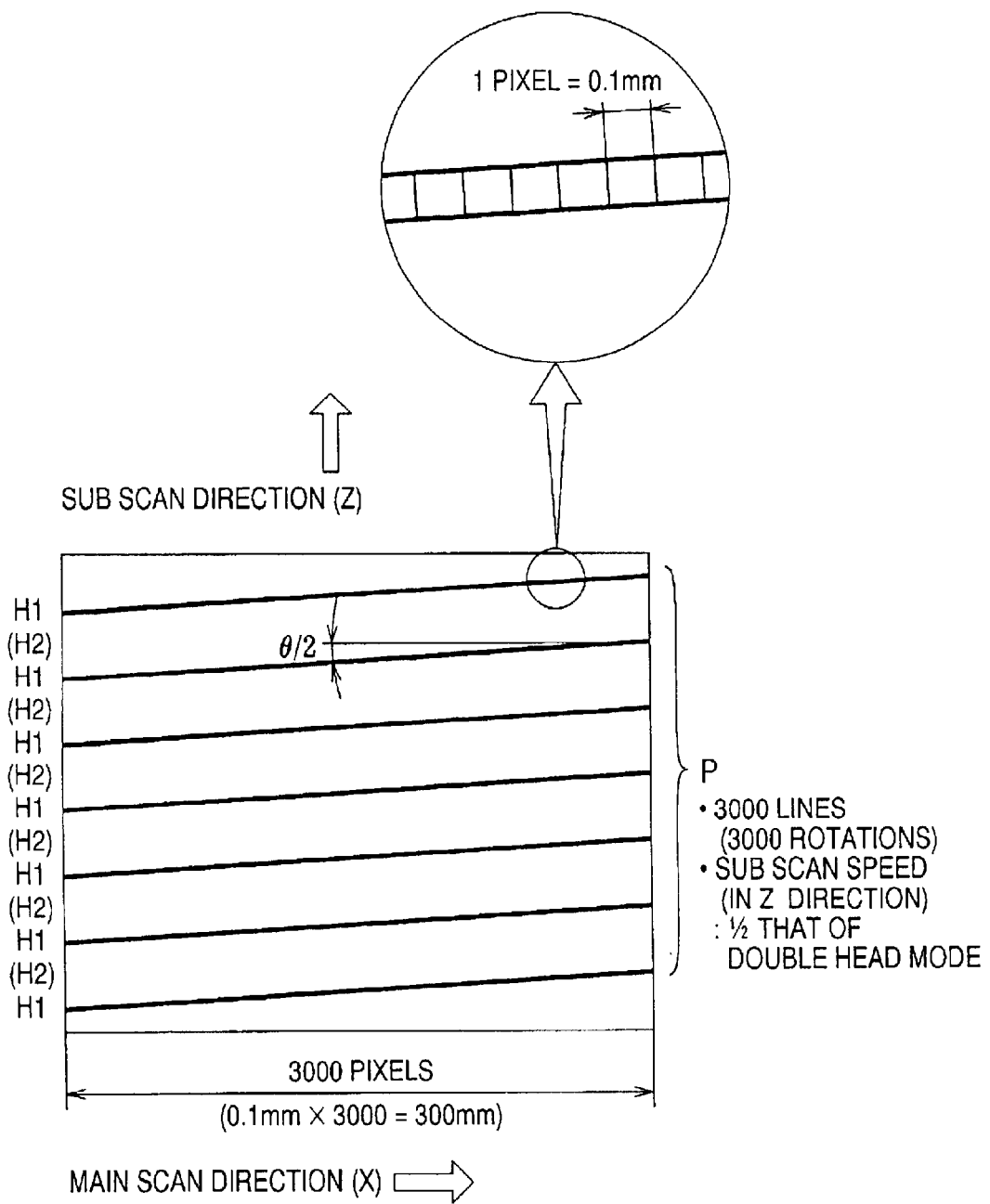
FIG. 8 illustrates a read scanning in a single-head mode operation of the X-ray image reader.

In the double head mode, the signal to the laser generator 27 is maintained in ON state as shown in the timing chart shown in FIG. 5 to always generate the laser light during the reading process. On the contrary, in the single head mode, the laser light is generated in only a time period from the generation of the EVEN signal to a generation of a next index signal, that is, in only a time for which the first read head H1 scans the X-ray image storing member 17, by sending the ON signal to the laser generator 27 for only that time period as shown in the timing chart shown in FIG. 5, such that laser light is not generated during a time period in which the second read head H2 scans the X-ray image storing member 17. Thus, as shown in FIG. 8, the reading process with the X-ray image-storing member 17 being irradiated with laser light is performed only when the first read head H1 scans the X-ray image-storing member 17, while the second read head H2 does not perform the reading process during the scan of the X-ray image-storing member 17.

In the single head mode, the moving speed of the X-ray image reader 1 in the sub scan direction shown by an arrow $\underline{G}$ is a half of that in the double head mode, while the rotation speed of the rotary mechanism 4 in the main scan direction is the same as that in the double head mode. Therefore, a tilting angle of the scan line in the single head mode is a half of the tilting angle $\theta$ of the scan line in the double head mode as shown in FIG. 7.

Since the moving speed of the X-ray image storing member 17 in the sub scan direction in the single head mode is a half of that in the double head mode, a reading time required to read the X-ray image storing member 17 having the same size becomes twice that in the case of the double head mode.

Incidentally, in the single head mode, the number of required scans and hence the number of scan lines is set to the same as that in the double head mode, that is, 3000. In the single head mode, one scan line is formed only by the first read head H1 in one rotation of the rotary mechanism 4 shown in FIG. 1. Therefore, in order to form 3000 scan lines, it is necessary to rotate the rotary mechanism 3000 times, that is, 2 times that in the double head mode.

During the scanning of the X-ray image-storing member 17 by the first read head H1, laser light from the laser light generator 27 shown in FIG. 1 passes through the first read head H1 and exposes the X-ray image-storing member 17 along the scan line $\underline{P}$ shown in FIG. 8. When there is a latent image of energy exists in the exposed portion of the X-ray image-storing member 17, the energy is excited by the laser light and emitted externally as light. The light emitted from the X-ray image-storing member 17 is received by the first read head H1 from which the laser light is emitted.

The light received by the read head is reflected by the dichroic mirror 26a in the head portion 7 of the rotary mechanism 4 to the first and second phototubes 16a and 16b of the photo detector 11 and signals corresponding to the lights are outputted from output terminals of the phototubes.

In the period during which the X-ray image storing member 17 is irradiated with laser light, the RESET signal is transmitted to the RESET terminal of the frequency divider circuit 51 of the pulse generator circuit 47 shown in FIG. 4 correspondingly to the EVEN signal outputted every rotation of the first read head H1 as shown in FIG. 5 and so single ENC-Z phase pulses and successive ENC-A phase pulses are outputted to the output terminal of the logic circuit 52.

The ENC-Z phase pulse is generated after a time tZ from the generation of the EVEN signal. On the other hand, the ENC-A phase pulse is successively generated in a time period from the generation of the ENC-Z phase pulse to a generation of a next index signal, that is, a time period during which the first read head H1 makes a half rotation corresponding an angle of 180 degrees. The frequency of the ENC-A phase pulse signal is 312.5 KHz, which is the output frequency of the frequency divider 51, and includes 3000 pulses during the half rotation of the read head corresponding to one scan line as shown in FIG. 6.

The intensity calculation circuit 48 shown in FIG. 4 reads the output of the phototube 16a or 16b for every pulse of the ENC-A phase pulse signal from the logic circuit 52. The read value is stored in a predetermined region of the RAM 43. In this manner, data for 1 pixel corresponding to one pulse of the ENC-A phase pulse signal is sampled. Since 3000 pulses of the ENC-A phase pulse signal are outputted for 1 scan line, the intensity calculation circuit 48 samples data for 3000 pixels obtained by dividing 1 scan line by 3000.

When the second read head H2 comes in the position opposing to the X-ray image storing member 17 after the data for 3000 pixels related to 1 scan line formed by the first read head H1 is sampled, there is neither ENC-Z phase pulse nor ENC-A phase pulse outputted as shown in the timing chart in FIG. 5. Further, in this case, the laser light irradiation by the second read head H2 is not performed. Therefore, the data acquisition by the second read head H2 is not performed.

Thereafter, the sampling of data for 3000 pixels in one scan line formed by one revolution of the first read head H1 is performed repeatedly, resulting in data for 3000 lines in the sub scan direction is sampled. In this manner, the light intensity data of the whole area of the measuring region of the X-ray image storing member 17 is read out as shown in FIG. 8 and the data is stored in a predetermined region of the RAM 43 correspondingly to the coordinates values of the X-ray image storing member 17 in the form of a data table.

According to the measurement in the single head mode, the reading operation is performed only by the first read head H1, while the data acquisition by the second read head H2 is not performed. Therefore, the problem of error due to the difference in reading characteristics between the first read head H1 and the second read head H2 in the double head mode is solved and it becomes possible to perform a very precise measurement.

Incidentally, in the single head mode, the ON/OFF operation of the laser generator 27 is performed every generation of the EVEN signal and the index signal as shown in FIG. 5. In this case, laser light having a rated intensity is not generated immediately even when the operation of the laser generator 27 is started in response to the ON signal and a certain time is required before the laser light output is stabilized at the rated intensity. This time is realized by the time $t_z$, which is provided between the generation of the EVEN signal and the generation of the ENC-A phase pulse and, in this embodiment, 400 $\mu$S corresponding to 122 pulses, as shown in FIG. 5.

(Other Embodiments)

Although the present invention has been described with reference to the preferred embodiments, the present invention is not limited thereto and can be modified in various manners within the scope of the present invention defined by the appended claims.

For example, in the embodiment shown in FIG. 1, the single head mode is realized by using only one of the two read heads, for example, the first read head H1, and the generation of laser light from the laser generator 27 is stopped when the other read head, that is, the second read head H2, scans the X-ray image storing member 17.

Figure 9:
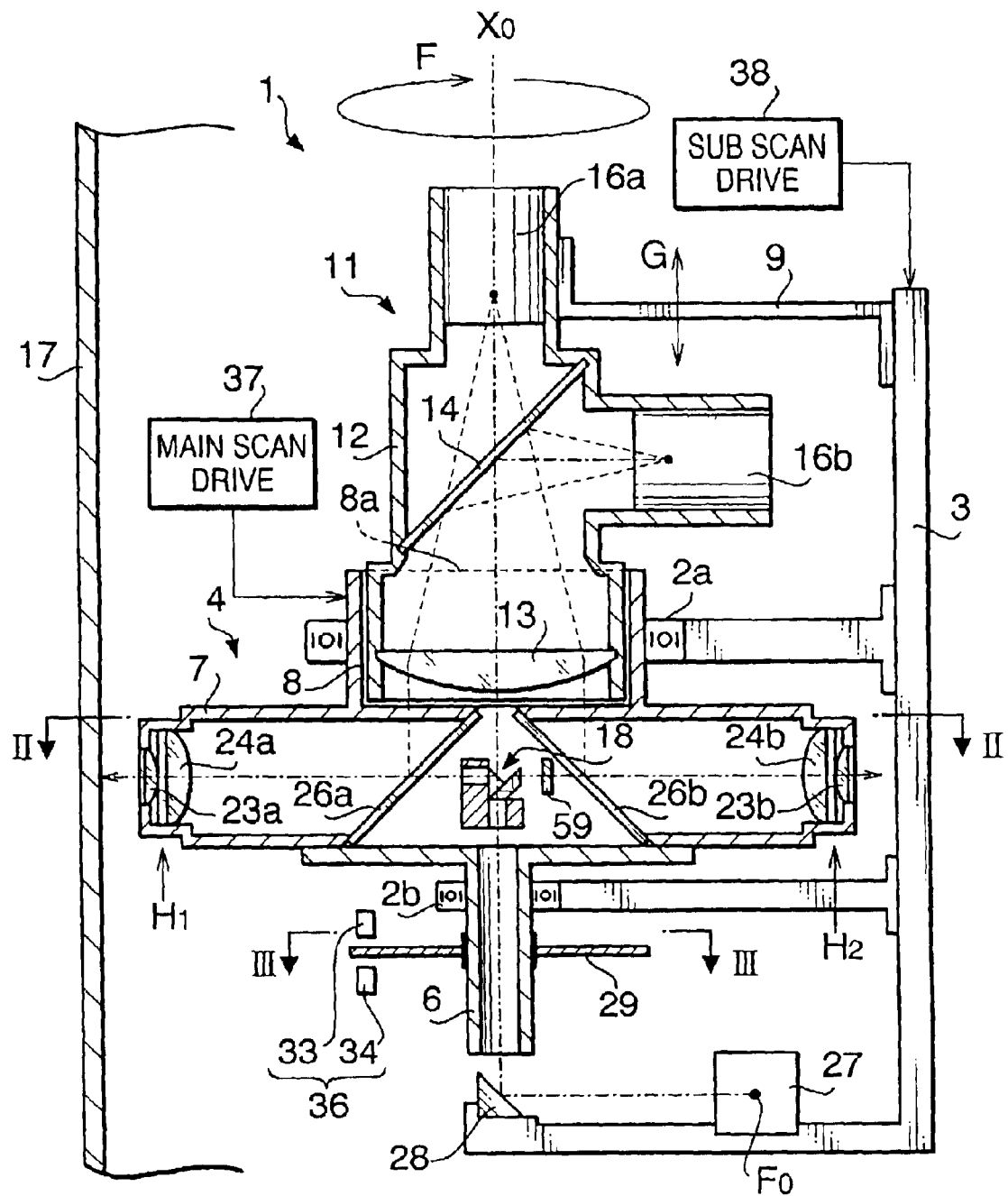
FIG. 9 is a cross section of an X-ray image reader according to another embodiment of the present invention.
Figure 10:
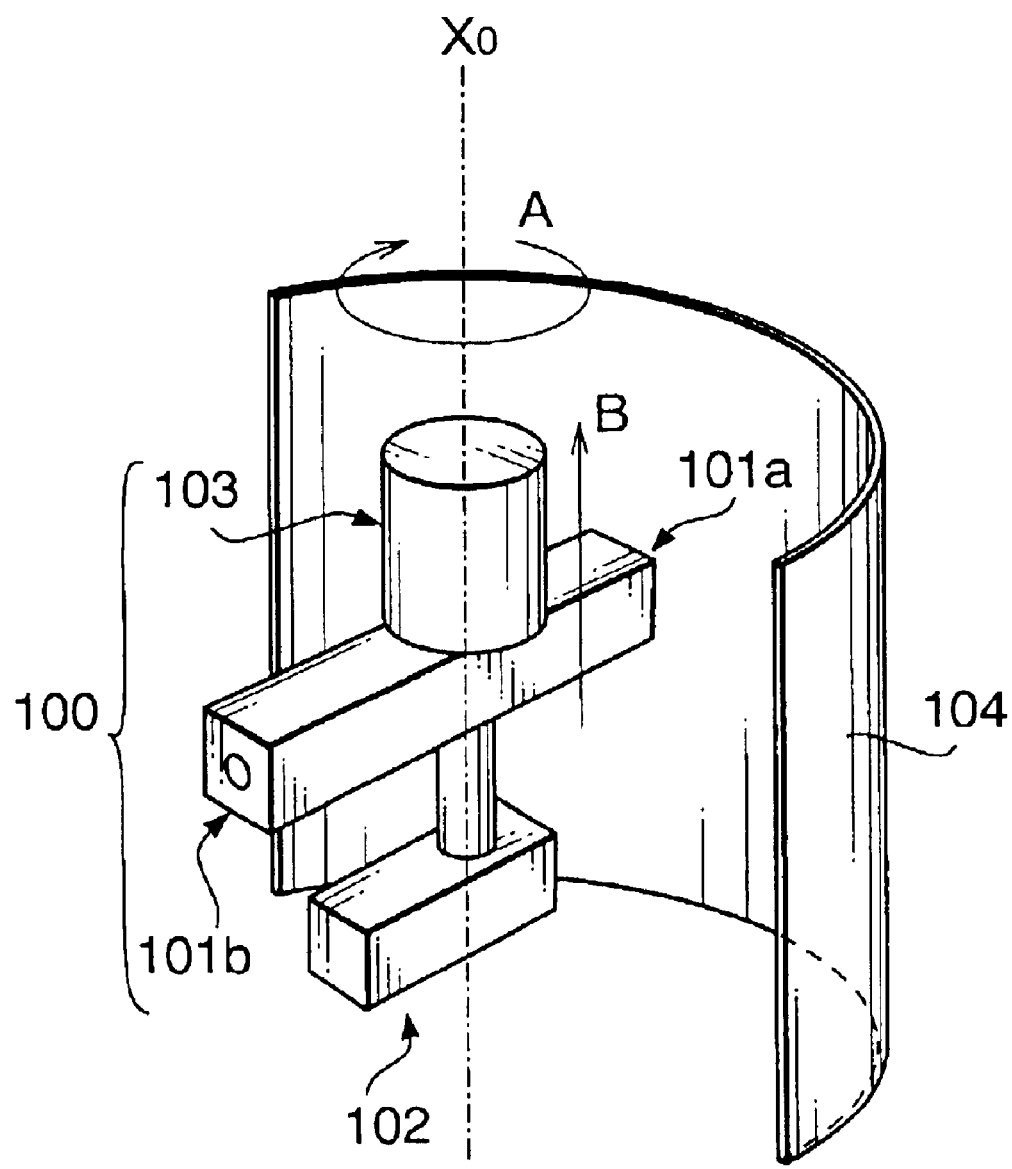
FIG. 10 is a perspective view of an example of a conventional X-ray image reader.

The means for making the second read head out of use is not limited to this scheme of stopping the generation of laser light. For example, a beam stopper or shutter 59 is provided on the optical path between the beam splitter 18 and the second read head H2 as shown in FIG. 9 to block laser light toward the second read head H2.

Further, although, in the described embodiments, the present invention is applied to the double head type X-ray image reader having two read heads, it is possible to apply the present invention to a multi head type X-ray image reader having three or more read heads.

What is claimed is:

1. An X-ray image reader comprising:
   a plurality of read heads;
   scan drive means for moving the plurality of said read heads to scan an X-ray image-storing member;
   first control means for performing a process for reading an X-ray image held on said X-ray image storing member by using at least two of said read heads; and
   second control means for performing a process for reading the X-ray image held on said X-ray image storing member by using any one of said read heads.

2. An X-ray image reader as claimed in claim 1, wherein said scan drive means moves the plurality of said read heads to a front of said X-ray image storing member alternatively to scan said X-ray image storing member.

3. An X-ray image reader as claimed in claim 2, wherein said scan drive means comprises:
   rotary drive means for rotating the plurality of said read heads; and
   straight drive means for moving the plurality of said read heads in a direction perpendicular to a plane of rotation of said read heads,
   wherein the plurality of said read heads are arranged in different angular positions in a direction of rotation thereof by said rotary drive means.

4. An X-ray image reader as claimed in claim 3, further comprising:
   a light emitting optical system for supplying emission-stimulating light to the plurality of said read heads;
   a light receiving optical system of receiving light emitted from said X-ray image storing member through the plurality of said read heads,
   wherein said X-ray image storing member has an X-ray storing surface formed of a storage fluorescent member, and wherein said second control means performs the reading processing by selection said any one of said read heads as a read head for supplying the emission stimulating light by said light emitting optical system.

5. An X-ray image reader as claimed in claim 4, wherein said second control means selects said any one of said read heads, which supplies the emission stimulating light by ON/OFF control of the generation of the emission stimulating light.

6. An X-ray image reader as claimed in claim 4, wherein said second control means selects said any one of said read head heads far supplying the emission stimulating light by arranging a beam stopper on only an optical path of said light emitting optical system for one other of said read heads, which is not used.

7. An X-ray image reader as claimed in claim 2, comprising:
   a light emitting optical system for supplying emission-stimulating light to the plurality of said read heads;
   a light receiving optical system for receiving light emitted from said X-ray image storing member through the plurality of said read heads,
   wherein said X-ray image storing member has an X-ray storing surface formed of a storage fluorescent member, and
   wherein said second control means performs the reading processing by selecting said any one of said read heads as a read head for supplying the emission stimulating light by said light emitting optical system.

8. An X-ray image reader as claimed in claim 7, wherein said second control means selects said any one of said read heads, which supplies the emission stimulating light by ON/OFF control of the generation of the emission stimulating light.

9. An X-ray image reader as claimed in claim 7, wherein said second control means selects said any one of said read heads for supplying the emission stimulating light by arranging a beam stopper on only an optical path of said light emitting optical system for one other of said read heads, which is not used.

10. An X-ray image reader as claimed in claim 1, further comprising:
    a light emitting optical system for supplying emission-stimulating light to the plurality of said read heads;
    a light receiving optical system for receiving light emitted from said X-ray image storing member through the plurality of said read heads,
    wherein said X-ray image storing member has an X-ray storing surface formed of a storage fluorescent member, and
    wherein said second control means performs the reading processing by selecting said any one of said read heads as a read head for supplying the emission stimulating light by said light emitting optical system.

11. An X-ray image reader as claimed in claim 10, wherein said second control means selects said any one of said read heads, which supplies the emission stimulating light by ON/OFF control of the generation of the emission stimulating light.

12. An X-ray image reader as claimed in claim 10, wherein said second control means selects said any one of said read head heads for supplying the emission stimulating light by arranging a beam stopper on only an optical path of said light emitting optical system for one other of said read heads, which is not used.

13. An X-ray image reader comprising:
    two read heads arranged with an angular interval of 180°;
    rotary drive means for rotating said two read heads;
    straight drive means for moving said two read heads in a direction perpendicular to a plane of rotation of said two read heads by said rotary drive means;
    first control means for performing a read processing of an X-ray image held on an X-ray image-storing member by using both of said two read heads;
    second control means for performing a read processing of the X-ray image held on said X-ray image storing member by using either one of said two read heads.

14. An X-ray image reader as claimed in claim 13, further comprising:
    a light emitting optical system for supplying emission stimulating light to said two read heads; and
    a light receiving optical system for receiving light emitted from said X-ray image storing member through said two read heads,
    wherein said X-ray image storing member has an X-ray storing surface formed of a storage fluorescent member, and
    wherein said second control means performs the read processing by selecting said either one of said two read heads as a read head for supplying the emission stimulating light by said light emitting optical system.

15. An X-ray image reader as claimed in claim 14, wherein said second control means selects said either one of said two read heads, which supplies the emission stimulating light by ON/OFF control of the generation of the emission stimulating light.

16. An X-ray image reader as claimed in claim 14, wherein said second control means selects said either one of said two read heads for supplying the emission stimulating light by arranging a beam stopper on only an optical path of said light emitting optical system for the other of said two read heads, which is not used.

* * * * *